United States Patent [19]

Henco et al.

[11] Patent Number: 5,652,141

[45] Date of Patent: Jul. 29, 1997

[54] DEVICE AND PROCESS FOR ISOLATING NUCLEIC ACIDS FROM CELL SUSPENSION

[75] Inventors: Karsten Henco, Erkrath; Metin Colpan, Essen-Kettwig; Petra Feuser, Cologne, all of Germany

[73] Assignee: Oiagen GmbH, Hilden, Germany

[21] Appl. No.: 442,100

[22] Filed: May 16, 1995

Related U.S. Application Data

[63] Continuation of Ser. No. 39,468, filed as PCT/EP91/02017, Oct. 24, 1991, abandoned.

[30] Foreign Application Priority Data

Oct. 26, 1990 [DE] Germany ............... 40 34 036.8

[51] Int. Cl.$^6$ ............... C12N 1/08; C12Q 1/68; C07H 1/06
[52] U.S. Cl. ............... 435/270; 435/6; 435/259; 536/12.7
[58] Field of Search ............... 435/6, 270, 288, 435/259; 536/127

[56] References Cited

U.S. PATENT DOCUMENTS 4,455,370 6/1984 Bartelsman et al. ............ 435/6
4,699,717 10/1987 Riesner et al. ............ 210/635
4,935,342 6/1990 Seligson et al. ............ 435/6
5,057,426 10/1991 Henco et al. ............ 435/270

FOREIGN PATENT DOCUMENTS 0268946 6/1988 European Pat. Off. .

OTHER PUBLICATIONS

Marieb, *Human Anatomy and Physiology*, Benjamin/Cummings, New York, 1992, p. 588.

Primary Examiner—Michael G. Wityshyn
Assistant Examiner—Francisco C. Prats
Attorney, Agent, or Firm—Jacobson, Price, Holman & Stern, PLLC

[57] ABSTRACT

A device and a process for isolating nucleic acids by lysing intact cells and removing nucleic acids emerging from the lysed cells by the following steps:

a) the cells are immobilized in a porous matrix, with the size of matrix voids being in the range of the type of cell to be lysed;
b) the cells are lysed;
c) the nucleic acids are fixated on the matrix surface, and subsequently
d) are eluted.

12 Claims, 1 Drawing Sheet

DEVICE AND PROCESS FOR ISOLATING NUCLEIC ACIDS FROM CELL SUSPENSION

This application is a continuation of application Ser. No. 08/039,468, filed as PCT/EP91/0207 Oct. 24, 1991, now abandoned.

This invention is directed to a process for isolating nucleic acids by lysing intact cells and removing nucleic acids emerging from the lysed cells, and to a device for performing said process.

Purification of nucleic acids plays a central role in modern molecular biology. Nucleic acids serve as starting materials for gene cloning and genetic analyses in laboratory diagnostic research and in routine use. For example, analysis of genetic diseases of blood cells, virus and bacterial analytics from blood, urine, faeces, and secretions are carried out on the basis of nucleic acids. Here, the analysis of whole blood is of particular clinical importance.

Conventionally, nucleic acids are recovered from cells. For this purpose, cells are digested, for instance, under severely denaturing and optionally reducing conditions (Maniatis, T., Fritsch, E. F. & Sambrook, S., 1982, Molecular Cloning: A Laboratory Manual, Cold Spring Harbor University Press, Cold Spring Harbor). Extensively used is digestion of cells using detergents as denaturing agents and the use of specific enzymes to degrade protein structures and enzymes which cleave nucleic acids. Thus, for example, sodium dodecylsulfate (SDS) and ethylenediamine tetraacetic acid (EDTA) are used as denaturing agents, and enzymes such as proteinase K. The result of such digestion procedure mostly is a highly viscous, gelatinous structure from which nucleic acids are isolated by phenol extraction. Here, the nucleic acids are preserved with great length and are removed from the aqueous phase subsequent to dialysis and precipitation. This digestion process is so aggressive that tissue fragments as well may be subjected to said process. However, due to the labor-intensive technique involving multiple replacements of reaction vessels, such method is unfavorable for large-scale sampling and routine preparations. While this process is capable of being automatized, a commercial apparatus, however, currently performs about 8 samples within four hours (Applied Biosystems A 371). Thus, the process is costly and is not suitable for passing samples in large series. Furthermore, it is disadvantageous that subsequent reactions such as enzymatic amplification are impaired due to the great length of the isolated nucleic acids. Moreover, the obtained solutions are highly viscous and difficult to handle. In particular, DNA of great length tends to interfere since nucleic acids recovered by the process according to prior art must be sheared separately in order to be further processed.

Digestion of cells in alkaline medium in the presence of detergents is technically simple but also results in nucleic acids of great length.

This crude preparation of nucleic acids is followed by subsequent reactions. These subsequent reactions require specific grade nucleic acids. Thus, the nucleic acid must be intact to the highest possible extent and the yield of preparation must be high and reproducible. The preparation route must be simple and economic and must offer possible automatization. Nucleic acid preparation must be possible without the risk of cross contamination of other samples, particularly where enzymatic amplification reactions such as Polymerase Chain Reaction (PCR) [Saiki, R., Gelfand, D. H., Stoffel, S., Scharf, S. J., Higuchi, R., Horn, G. T., Mullis, K. B. & Erlich, H. A. (1988), Science 239, 487–491] and Ligase Chain Reaction (LCR) (EP-A-88 311 741.8) are employed. Therefore, it is desirable to obtain the nucleic acids with not too great a chain length, to digest the cells as quantitative as possible, and for what remains, to avoid the above-mentioned disadvantages of digestion processes known in prior art.

Thus, the technical problem which this invention is based upon is to provide an improved process for isolating nucleic acids from intact cells; in particular, the obtained nucleic acid should not exhibit excessive chain length, should be isolable using a few steps, and should offer the possibility of being subjected directly to the subsequent reactions required.

This technical problem is solved by a process for isolating nucleic acids by lysing intact cells and removing the nucleic acids emerging from the lysed cells, characterized in that a) the cells are immobilized in a porous matrix, with the size of matrix voids being in the range of the type of cell to be lysed;
 b) the cells are lysed;
 c) the nucleic acids are fixated on the matrix surface, and subsequently
 d) are eluted.

Preferably, the matrix consists of porous inorganic or organic polymers, with the surface properties of the material, binding the matrix providing for reversible or irreversible immobilization of cells at the surface. Preferably, the void size of the material forming the matrix is from 1 to 50 µm. Particularly preferred are void sizes of from 5 to 15 µm. This can be accomplished in a preferred embodiment of the process according to the invention wherein the particle size of the material forming the matrix is from 10 to 50 µm, preferably from 15 to 25 µm.

The cells immobilized within the matrix are lysed preferably by physical or chemical action where lysis either may be effected mechanically such as by ultrasonic waves or by shear forces, osmotic shock, or chemically using detergents or alkaline digestion.

In a particularly preferred embodiment, the surface of the material forming the matrix has ion exchanging properties. Especially when using anion exchangers the nucleic acid emerging from the lysed cell may be bound reversibly to the material forming the matrix to be eluted by adjusting to high ionic strengths subsequent to various washing operations.

BRIEF DESCRIPTION OF THE DRAWING

The FIGURE illustrates a preferred embodiment of the device according to the invention.

The procedure according to the invention results in preparation of nucleic acids of high purity and permits to perform analytics reproducible qualitatively and quantitatively, particularly in combination with enzymatic processes for the amplification of nucleic acids. It has turned out that mild digestion methods using detergents or physical digestion methods such as heating a sample facilitates subsequent applications. For instance, when using the process according to the invention, cellular DNA shorter in length (<200 kb) and total nucleic acids, respectively, are obtained from the cell. The reasons for such limited nucleic acid cleavage are not completely known. However, the mild digestion methods appear to result in partial degradation of the nucleic acid.

Figure 1:
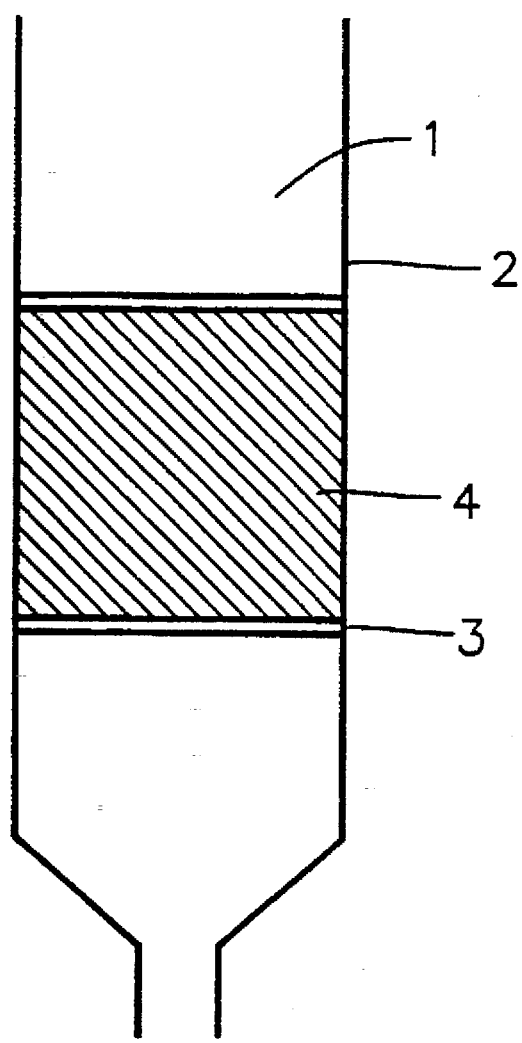

For such reproducible procedure it is advantageous to use a matrix having ion exchanging properties so that liberated nucleic acids can adhere to this surface and are out of reach for degrading enzymes. Then, nucleic acids of nearly ideal length for subsequent reactions such as PCR are recovered.

For example, if white blood cells from mammals are to be digested, erythrocytes free of DNA must be removed first. To do this, various processes are known such as, e.g., gradient centrifugation or extraction of cells using surface-coupled antibodies (anti-HLA magnetobeads). It has proven particularly advantageous to agglomerate the erythrocytes using dextran and remove them without centrifugation. The supernatant contains the other blood cells and less than 1/100 of the initial erythrocyte concentration. Then, the white blood cells are transferred from the suspension into the pores of the matrix using the process according to the invention. This is effected by pressure difference or centrifugation forces. It has turned out that it is not sufficient to concentrate the cells, for instance, by simple centrifugation, by forming a pellet, or by filtration through narrow-mesh membranes since then, cell digestion according to the invention is no longer effected reliably. Cell formations thereby produced, being relatively dense and having direct cell-to-cell contact can be digested only insufficiently when using these mild non-ionic agents. Probably, merely those cells are lysed which are located at the surface of such a cell concentrate.

By the process according to the invention, it is ensured that such pelletization does not occur. Here, the cells are concentrated by a type of deep bed filtration within the matrix, i.e., are captured in a small volume element. This means that the cells are arranged within the matrix in virtually isolated fashion but do not lie on top of each other. According to the invention, this is achieved by using a porous matrix, for example, a particle bed, the interstices of which being in the range of the cell size. Then, the cells penetrate the matrix to a certain depth.

In a preferred embodiment of the process according to the invention, silica gel particles are employed having a particle size of preferably from 15 to 25 μm so that grain interspacings of from 1 to 50 μm are formed. The average size of erythrocytes is 2 μm, of lymphocytes approximately 8 μm, and of monocytes about 15 μm.

In another preferred embodiment of the process according to the invention, particles are used for immobilizing which are embedded in an inert network of membranes, preferably Teflon, the interstices again corresponding approximately to the dimensions of the cells to be lysed. Thereby, it is ensured that the cells preferably are seized within the network and do not—as for instance on a sterile filter—deposit densely packed in the form of a filter cake.

Between the cells, narrow channels remain through which solutions can be interchanged such as, for instance, serum for cell-lysing solution. Since all the cells are accessible for reagents, said mild lysing conditions may be used without the danger of losses in yield.

In a particularly preferred embodiment, the particles have ion exchanging properties as described, for example, in DE-PS 32 11 305. For the membrane-based embodiment, an ion exchanger on the basis of silica gel with particle sizes of between 15 and 25 μm and pore sizes of 1500 Å has proven particularly useful. Due to direct spatial contact to all the lysing cells, it is ensured that the DNA, subsequent to lysis and partial degradation, is directly fixed at the surface of the solid phase and thus, is protected against further nuclease attack. In this condition, contaminants may be washed out readily, followed by eluting the purified nucleic acid in a small volume. In this fashion, reproducible chain lengths of from 5 to 20 kb on average are obtained. Under the digestion conditions as described in the example, less than 10% is shorter than 5 kb. This represents optimum length distribution for subsequent enzymatic nucleic acid amplification.

Likewise surprisingly, it has been determined that the desired size distribution is achieved in leukocyte preparation using dextran while preparation over Ficoll in the gradient usually results in shorter fragments (500 to 1000 bp).

It has turned out that the process according to the invention may be conducted in particularly favorable fashion by means of the device claimed according to the invention and to be described in the following. The device according to the invention consists of a hollow body (1) wherein the matrix (4) accomodating the cells is arranged between two porous units (2, 3). The pore size of the units 2, 3, preferably polyethylene or glass frits, must be larger than the void size of the material forming the matrix 4. The units 2, 3 have a pore size of from 50 to 100 μm, with the void size of the material forming the matrix 4 being about from 1 to 50 μm. Matrix 4 is a net-like membrane having a multitude of pores of from 1 to 50 μm in size and in addition, ion exchanger particles. The cells are then immobilized within the free pores, with the liberated nucleic acids being adsorbed on the ion exchanger particles situated in said matrix.

A likewise preferred embodiment is represented by a device where the material forming the matrix 4 is a particulate organic or inorganic polymer. Preferably, the material forming the matrix 4 is a silica gel having ion exchanging properties and a particle size of from 15 to 25 μm.

The FIGURE illustrates a preferred embodiment of the device according to the invention. For exmple, the hollow body 1 may be a commercial tubing (MoBiCol, MoBiTec, Göttingen or Millipore UFC3 OHW25). Between two narrowly inserted units 2, 3, for example, polyethylene frits having a pore size of from 50 to 100 μm, there is situated a membrane having pores of from 5 to 10 μm in size and likewise containing silica gel (pore size 1500 Å, particle size 15 μm) having anion exchanging properties. The membrane has a thickness of about 1 mm. The capacity of the ion exchanger material is about 15 μg of DNA. Of course, the capacity for DNA may be increased by stacking corresponding membranes onto one another. With low mechanical lead, edge welding or cementing the membrane is possible whereby the stabilizing effect of units 2, 3 may be dropped so that the membrane seals the hollow body 4 without said units.

Likewise, it is possible to fill small columns with the described silica gel arranged between 2 polyethylene frits having a pore size of 35 μm. Preferably, the upper unit 2 is chosen with larger pores (70 μm). The MoBiCol columns are charged with about 70 mg of ion exchanger gel corresponding to a filling height of 3 mm. With respect to plasmid DNA, a capacity of 150 μg of DNA results.

EXAMPLE

Cellular DNA Preparation from Blood

To 6 ml of citrate blood in a 12 ml PPN tube is homogeneously added 0.12 g of dextran (MW 250,000) and incubated at room temperature for 60 minutes. Dextran and erythrocytes form aggregates which sediment within 45 minutes. The pale supernatant contains leukocytes in approximately natural composition [(1–5)×10$^6$ leukocytes/ml, erythrocytes/leukocytes ca. 2/1]. 0.5 ml of this supernatant is applied to the device and passed through the filter by centrifugation or pressure. The cells are retained in the network. After passage of the serum, washing is effected using 1×0.5 ml of washing solution (PBS 120 mM NaCl, 2.7 mM KCl, 10 mM KPi pH 7.4) (phosphate buffered saline).

Thereafter, the cells are lysed using 125 μl of a 1% solution of non-ionic detergent (NP40; Tween 20). Impurities are washed out using 0.5 ml of 750 mM KCl, 50 mM of MOPS pH 7.0, 15% ethanol. DNA is eluted using either high saline buffer (1.2M KCl, 50 mM MOPS, pH 7.0) or alkali buffer (200 mM KOH). The advantage of the alkali buffer consists in that subsequent to buffer addition for neutralization, direct enzymatic amplification may be effected, for example, without the necessity of initial nucleic acid precipitation. However, there is a risk of DNA damage. In many cases, an aliquot of the high saline elution may be used directly if the required nucleic acid concentration is present.

What is claimed is:

1. A process for isolating nucleic acids by lysing blood cells, substantially all of which are intact, and removing the nucleic acids emerging from the lysed cells, comprising the steps of:
    a) immobilizing the cells in a porous matrix having ion exchange properties and having voids each having a size sufficient to capture one of the cells;
    b) lysing the cells;
    c) fixing the emerging nucleic acids on the matrix surface by ion exchange, and subsequently;
    d) eluting the nucleic acids.

2. The process according to claim 1, wherein the matrix has a void size of from 1 to 50 µm.

3. The process according to claim 2, wherein the void size is from 5 to 15 µm.

4. The process according to claim 1, wherein the porous matrix comprises particles each having a particle size of 10 to 50 µm.

5. The process according to claim 4, wherein the particle size is from 15 to 25 µm.

6. The process according to claim 1, wherein the cell lysing is effected by ultrasonic waves, shear forces, detergents, enzymes, osmotic shock, or combinations thereof.

7. The process according to claim 1, wherein the nucleic acids are eluted by a buffer or by alkaline elution.

8. The process according to claim 1, wherein said matrix is washed between at least one of steps a) and b), and b) and c), and c) and d).

9. The process according to claim 1, wherein the matrix is an inorganic or organic polymer.

10. The process according to claim 9, wherein the matrix has a void size of from 1 to 50 µm.

11. The process according to claim 10, wherein the void size is from 5 to 15 µm.

12. In a process for isolating nucleic acids by lysing blood cells and removing the nucleic acids emerging from the lysed cells, the improvement comprising the steps of:
    a) before lysing, immobilizing the blood cells in a porous matrix having ion exchange properties and having voids each having a size sufficient to capture one of the cells;
    b) lysing the captured cells;
    c) fixing the emerging nucleic acids on the matrix surface by ion exchange, and subsequently;
    d) eluting the nucleic acids.

* * * * *